US011167026B2

(12) United States Patent
Wagner et al.

(10) Patent No.: US 11,167,026 B2
(45) Date of Patent: Nov. 9, 2021

(54) STIMULATION OF NEONATAL IMMUNITY AGAINST EHV-1

(71) Applicant: CORNELL UNIVERSITY, Ithaca, NY (US)

(72) Inventors: Bettina Wagner, Ithaca, NY (US); Gillian Perkins, Freeville, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/036,257

(22) PCT Filed: Nov. 12, 2014

(86) PCT No.: PCT/US2014/065168
§ 371 (c)(1),
(2) Date: May 12, 2016

(87) PCT Pub. No.: WO2015/073507
PCT Pub. Date: May 21, 2015

(65) Prior Publication Data
US 2016/0263211 A1    Sep. 15, 2016

Related U.S. Application Data

(60) Provisional application No. 61/903,619, filed on Nov. 13, 2013.

(51) Int. Cl.
| *A61K 39/245* | (2006.01) |
| *A61K 39/12* | (2006.01) |
| *A61K 39/42* | (2006.01) |
| *C07K 14/005* | (2006.01) |
| *C07K 14/54* | (2006.01) |
| *C12N 7/00* | (2006.01) |
| *A61K 39/00* | (2006.01) |

(52) U.S. Cl.
CPC ............ *A61K 39/245* (2013.01); *A61K 39/12* (2013.01); *A61K 39/42* (2013.01); *C07K 14/005* (2013.01); *C07K 14/5406* (2013.01); *C12N 7/00* (2013.01); *A61K 2039/505* (2013.01); *A61K 2039/54* (2013.01); *A61K 2039/542* (2013.01); *A61K 2039/545* (2013.01); *A61K 2039/55* (2013.01); *A61K 2039/552* (2013.01); *A61K 2039/55527* (2013.01); *A61K 2039/575* (2013.01); *C07K 2319/00* (2013.01); *C12N 2710/16034* (2013.01); *C12N 2710/16734* (2013.01)

(58) Field of Classification Search
CPC .................. A61K 39/245; A61K 39/12; A61K 2039/552; C07K 14/5406; C07K 2319/00
See application file for complete search history.

(56) References Cited

U.S. PATENT DOCUMENTS

| 7,892,533 B2 | 2/2011 | Suter et al. |
| 2005/0220767 A1 | 10/2005 | Collins et al. |
| 2011/0274649 A1 | 11/2011 | Kupper et al. |
| 2011/0287454 A1 | 11/2011 | Wagner |
| 2012/0195893 A1 | 8/2012 | Casares et al. |
| 2013/0251747 A1 | 9/2013 | Audonnet et al. |

OTHER PUBLICATIONS

Thara et al. Vaccine therapy with sipuleucel-T (Provenge) for prostate cancer. Maturitas. Aug. 2011;69(4):296-303.*
Kim et al. Cytokine Molecular Adjuvants Modulate Immune Responses Induced by DNA Vaccine Constructs for HIV-1 and SIV. J Interferon Cytokine Res. Jan. 1999;19(1):77-84.*
McCormick et al. Immunization with an Interferon-g-gp120 Fusion Protein Induces Enhanced Immune Responses to Human Immunodeficiency Virus gp120. J Infect Dis. Dec. 1, 2001;184(11):1423-30.*
Heath et al. Cytokines as immunological adjuvants. Vaccine. 1992;10(7):427-34.*
International Search Report dated Apr. 28, 2015 issued in PCT/US2014/065168.
Adkins B., "T-Cell Function in Newborn Mice and Humans", Immunology Today 20(7):330-335 (Jul. 1999).
Arulanandam B.P. et al., "Neonatal Administration of IL-12 Enhances the Protective Efficacy of Antiviral Vaccines", The Journal of Immunology 164:3698-3704 (2000).
Breathnach C.C. et al., "Foals are Interferon Gamma-Deficient at Birth", Veterinary Immunology and Immunopathology 112:199-209 (2006).
Boyd N.K. et al., "Temporal Changes in Cytokine Expression of Foals During the First Month of Life", Veterinary Immunology and Immunopathology 92:75-85 (2003).
Elia G. et al., "Detection of Equine Herpesvirus Type 1 by Real Time PCR", Journal of Virological Methods 133:70-75 (2006).
Falcone FH et al., "The 21st Century Renaissance of the Basophil? Current Insights into its Role in Allergic Responses and Innate Immunity", Experimental Dermatology 15:855-864 (2006).
Foote C.E. et al., "Detection of EHV-1 and EHV-4 DNA is Unweaned Throughbred Foals from Vaccinated Mares on a Large Stud Farm", Equine Veterinary Journal 36(4):341-345 (2004).
Gessner A. et al., "Mast Cells, Basophils, and Eosinophils Acquire Constitutive IL-4 and IL-13 Transcripts During Lineage Differentiation That are Sufficient for Rapid Cytokine Production", The Journal of Immunology 174:1063-1072 (2005).
Gilkerson J.R. et al., "Epidemiological Studies of Equine Herpesvirus 1 (EHV-1) in Thoroughbred Foals: A Review of Studies Conducted in the Hunter Valley of New South Wales Between 1995 and 1997", Veterinary Microbiology 68:15-25 (1999).

(Continued)

*Primary Examiner* — Dong Jiang
(74) *Attorney, Agent, or Firm* — Scully, Scott, Murphy & Presser, P.C.

(57) ABSTRACT

The present invention provides methods for inducing an immune response to a pathogen in neonatal mammals. In particular, the present invention provides methods for inducing an immune response to a pathogen in a neonatal mammal comprising administering to the neonatal mammal a composition comprising a fusion protein between interleukin-4 (IL-4) and a first antigen of the pathogen.

Figure 1:
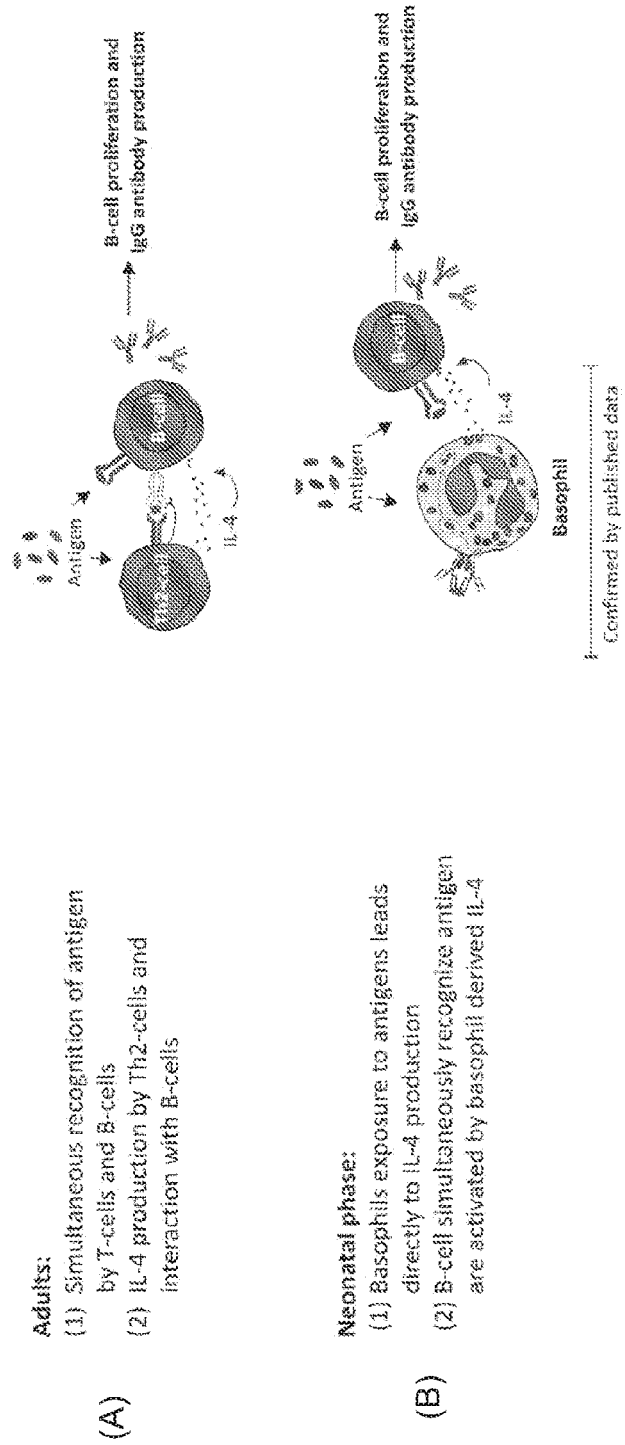

32 Claims, 5 Drawing Sheets
Specification includes a Sequence Listing.

(56) References Cited

OTHER PUBLICATIONS

Goehring L.S. et al., "Equine Herpesvirus Type 1-Associated Myeloencephalopathy in the Netherlands: A Four-Year Retrospective Study (1999-2003)", J. Vet Intern Med. 20:601-607 (2006).
Goodman L.B. et al., "Comparison of the Efficacy of Inactivated Combination and Modified-Live Virus Vaccines Against Challenge Infection With Neuropathogenic Equine Herpesvirus Type 1 (EHV-1)", Vaccine 24:3636-3645 (2006).
Goodman L.B. et al., "A Point Mutation in a Herpesvirus Polymerase Determines Neuropathogenicity", pLoS Pathogens 3(11):e160, pp. 1583-1592 (Nov. 2007).
Holznagel D.L. et al., "Onset of Immunoglobulin Production in Foals", Equine Veterinary Journal 35(6):620-622 (2003).
Jacks S. et al., "Experimental Infection of Neonatal Foals With Rhodococcus Equi Triggers Adult-Like Gamma Interferon Induction", Clinical and Vaccine Immunology 14(6):669-677 (Jun. 2007).
Kabithe E et al., "Monoclonal Antibodies to Equine CD14", Veterinary Immunology and Immunopathology 138:149-153 (2010).
Keggan A. et al., "Production of Seven Monoclonal Equine Immunoglobulins Isotyped by Multiplex Analysis", Veterinary Immunology and Immunopathology 153:187-193 (2013).
Kydd J.H. et al., "The Equine Immune Response to Equine Herpesvirus-1: The Virus and its Vaccines", Veterinary Immunology and Immunopathology 111:15-30 (2006).
Kydd J.H. et al., "Distribution of Equid Herpesvirus-1 (EVH-1) in Respiratory Tract Associated Lymphoid Tissue: Implications for Cellular Immunity", Equine Veterinary Journal 26(6):470-473 (1994).
Lunn D.P. et al., "Equine Herpesvirus-1 Consensus Statement", J Vet Intern Med 23:450-461 (2009).
Mack M. et al., "Identification of Antigen-Capturing Cells as Basophils", The Journal of Immunology 174:735-741 (2005).
Mealey R.H. et al., "Experimental Rhodococcus Equi and Equine Infectious Anemia Virus DNA Vaccination in Adult and Neonatal Horses: Effect of IL-12,I Dose, and Route", Vaccine 25:7582-7597 (2007).
Min B. et al., "Basophils Produce IL-4 and Accumulate in Tissues After Infection With a Th2-Inducing Parasite", The Journal of Experimental Medicine 200(4):507-517 (Aug. 16, 2004).
Morein B. et al., "Immune Responsiveness in the Neonatal Period", J. Comp. Path. 137:S27-S31 (2007).
Noronha L.E. et al., "Generation and Characterization of Monoclonal Antibodies to Equine CD16", Veterinary Immunology and Immunopathology 146:135-142 (2012).
Nugent J. et al., "Analysis of Equid Herpesvirus 1 Strain Variation Reveals a Point Mutation of the DNA Polymerase Strongly Associated With Neuropathogenic Versus Nonneuropathogenic Disease Outbreaks", Journal of Virology 80(8):4047-4060 (Apr. 2006).
Oh K. et al., "Induction of Th2 Type Immunity in a Mouse System Reveals a Novel Immunoregulatory Role of Basophils", Blood 109(7):2921-2927 (Apr. 1, 2007).
Paillot R. et al., "Frequency and Phenotype of EHV-1 Specific, IFN-y Synthesising Lymphocytes in Ponies: The Effects of Age, Pregnancy and Infection", Developmental & Comparative Immunology 31:202-214 (2007).
Paillot R. et al., "Equine Interferon Gamma Synthesis in Lymphocytes After In Vivo Infection and In Vitro Stimulation With EHV-1", Vaccine 23:4541-4551 (2005).
Patel J.R. et al., "Equine Herpesviruses 1 (EHV-1) and 4 (EHV-4)—Epidemiology, Disease and Immunoprophylaxis: A Brief Review", The Veterinary Journal 170:14-23 (2005).
Paul W.E., "Interleukin 4/B Cell Stimulatory Factor 1: One Lymphokine, Many Functions", FASEB J. 1:456-461 (1987).
Perkins G.A. et al., "Investigation of the Prevalence of Neurologic Equine Herpes Virus Type 1 (EHV-1) in a 23-Year Restrospective Analysis (1984-2007)", Veterinary Microbiology 139:375-378 (2009).
Quah B.J.C. et al., "Monitoring Lymphocyte Proliferation In Vitro and In Vivo With the Intracellular Fluorescent Dye Carboxyfluorescein Diacetate Succinimidyl Ester", Nature Protocols 2(9):2049-2056 (2007).
Scheper T. et al., "The Glycoproteins C and G are Equivalent Target Antigens for the Determination of Herpes Simplex Virus Type 1-Specific Antibodies", Journal of Virological Methods 166:42-47 (2010).
Sheoran A.S. et al., "Immunoglobulin Isotypes in Sera and Nasal Mucosal Secretions and Their Neonatal Transfer and Distribution in Horses", AJVR 61(9):1099-1105 (Sep. 2000).
Slater J.D. et al., "The Trigeminal Ganglion in a Location for Equine Herpesvirus 1 Latency and Reactivation in the Horse", Journal of General Virology 75:2007-2016 (1994).
Soboll Hussey G. et al., "Evaluation of Immune Responses Following Infection of Ponies With an EHV-1 ORF1/2 Deletion Mutant", Veterinary Research 42:23 (12 pages) (2011).
Sokol C.L. et al., "A Mechanism for the Initiation of Allergen-Induced T Helper Type 2 Responses", Nature Immunology 9(3):310-318 (Mar. 2008).
Wagner B. et al., "Monoclonal Antibodies to Equine CD23 Identify the Low-Affinity Receptor for IgE on Subpopulations of IgM+ and IgG1+ Be-Cells in Horses", Veterinary Immunology and Immunopathology 146:125-134 (2012).
Wagner B. et al., "Infection of Peripheral Blood Mononuclear Cells With Neuropathogenic Equine Herpesvirus Type-1 Strain Ab4 Reveals Intact Interferon-a Induction and Induces Suppression of Anti-Inflammatory Interleukin-10 Responses in Comparison to Other Viral Strains", Veterinary Immunology and Immunopathology 143:116-124 (2011).
Wagner B. et al., "Induction of Interleukin-4 Production in Neonatal IgE+ Cells After Crosslinking of Maternal IgE", Developmental and Comparative Immunology 34:436-444 (2010).
Wagner B. et al., "Interferon-Gamma, Interleukin-4 and Interleukin-10 Production by T Helper Cells Reveals Intact Th1 and Regulatory TR1 Cell Activation and a Delay of the Th2 Cell Response in Equine Neonates and Foals", Vet. Res. 41:47 (2010).
Wagner B. et al., "Development of a Bead-Based Multiplex Assay for Simultaneous Quantification of Cytokines in Horses", Veterinary Immunology and Immunopathology 127:242-248 (2009).
Wagner B. et al., "Occurrence of IgE in Foals: Evidence for Transfer of Maternal IgE by the Colostrum and Late Onset of Endogenous IgE Production in the Horse", Veterinary Immunology and Immunopathology 110:269-278 (2006).
Wagner B. et al., "Monoclonal Anti-Equine IgE Antibodies With Specificity for Different Epitopes on the Immunoglobulin Heavy Chain of Native IgE", Veterinary Immunology and Immunopathology 92:45-60 (2003).
Lauring A.S. et al., "Rationalizing the development of live attenuated virus vaccines", Nat Biotechnol., (2010), 28(6), pp. 573-579 doi:10.1038/nbt.1635.

\* cited by examiner

FIG. 2

SEQUENCE LISTING

<160> NUMBER OF SEQ ID NOS: 7

<210> SEQ ID NO 1
<211> LENGTH: 462
<212> TYPE: DNA
<213> ORGANISM: Homo sapiens

<400> SEQUENCE: 1

| | |
|---|---|
| atgggtctca cctcccaact gcttcccct ctgttcttcc tgctagcatg tgccggcaac | 60 |
| tttgtccacg gacacaagtg cgatatcacc ttacaggaga tcatcaaaac tttgaacagc | 120 |
| ctcacagagc agaagactct gtgcaccgag ttgaccgtaa cagacatctt tgctgcctcc | 180 |
| aagaacacaa ctgagaagga aaccttctgc agggctgcga ctgtgctccg gcagttctac | 240 |
| agccaccatg agaaggacac tcgctgcctg ggtgcgactg cacagcagtt ccacaggcac | 300 |
| aagcagctga tccgattcct gaaacggctc gacaggaacc tctggggcct ggcgggcttg | 360 |
| aattcctgtc ctgtgaagga agccaaccag agtacgttgg aaaacttctt ggaaaggcta | 420 |
| aagacgatca tgagagagaa atattcaaag tgttcgagct ga | 462 |

<210> SEQ ID NO 2
<211> LENGTH: 153
<212> TYPE: PRT
<213> ORGANISM: Homo sapiens

<400> SEQUENCE: 2

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 3
<211> LENGTH: 423
<212> TYPE: DNA
<213> ORGANISM: Mus musculus

<400> SEQUENCE: 3

| | |
|---|---|
| atgggtctca cccccagct agttgtcatc ctgctcttct ttctcgaatg taccaggagc | 60 |
| catatccacg gatgcgacaa aaatcacttg agagagatca tcggcatttt gaacgaggtc | 120 |
| acaggagaag ggacgccatg cacggagatg gatgtgccaa acgtcctcac agcaacgaag | 180 |
| aacaccacag agagtgagct cgtctgtagg gcttccaagg tgcttcgcat attttattta | 240 |

```
aaacatggga aaactccatg cttgaagaag aactctagtg ttctcatgga gctgcagaga    300
ctctttcggg cttttcgatg cctggattca tcgataagct gcaccatgaa tgagtccaag    360
tccacatcac tgaaagactt cctggaaagc ctaaagagca tcatgcaaat ggattactcg    420
tag                                                                  423

<210> SEQ ID NO 4
<211> LENGTH: 140
<212> TYPE: PRT
<213> ORGANISM: Mus musculus

<400> SEQUENCE: 4

Met Gly Leu Asn Pro Gln Leu Val Val Ile Leu Leu Phe Phe Leu Glu
1               5                   10                  15

Cys Thr Arg Ser His Ile His Gly Cys Asp Lys Asn His Leu Arg Glu
            20                  25                  30

Ile Ile Gly Ile Leu Asn Glu Val Thr Gly Glu Gly Thr Pro Cys Thr
        35                  40                  45

Glu Met Asp Val Pro Asn Val Leu Thr Ala Thr Lys Asn Thr Thr Glu
    50                  55                  60

Ser Glu Leu Val Cys Arg Ala Ser Lys Val Leu Arg Ile Phe Tyr Leu
65                  70                  75                  80

Lys His Gly Lys Thr Pro Cys Leu Lys Lys Asn Ser Ser Val Leu Met
                85                  90                  95

Glu Leu Gln Arg Leu Phe Arg Ala Phe Arg Cys Leu Asp Ser Ser Ile
            100                 105                 110

Ser Cys Thr Met Asn Glu Ser Lys Ser Thr Ser Leu Lys Asp Phe Leu
        115                 120                 125

Glu Ser Leu Lys Ser Ile Met Gln Met Asp Tyr Ser
    130                 135                 140

<210> SEQ ID NO 5
<211> LENGTH: 414
<212> TYPE: DNA
<213> ORGANISM: Equus caballus

<400> SEQUENCE: 5
atgggtctca cctaccaact gcttccagct ctggtctgct tactagcatg taccagcaac     60
ttcatccagg gatgcaaata cgacatcacc ttacaagaga tcatcaaaac gctgaacaac    120
ctcacagatg gaaagggcaa gaattcgtgc atggagctga ctgtagcgga tgcctttgct    180
ggcccgaaga acacagatgg aaaggaaatc tgcagggctg caaaggtgct tcaacagctc    240
tataaaagac atgacaggtc cttgatcaaa gaatgcctga gcggactgga caggaacctc    300
aagggcatgg caaacgggac ctgctgtact gtgaatgaag ccaagaagag cacattgaaa    360
gactttttgg aaaggctaaa gacgatcatg agagagaaat actccaagtg ttga          414

<210> SEQ ID NO 6
<211> LENGTH: 137
<212> TYPE: PRT
<213> ORGANISM: Equus caballus

<400> SEQUENCE: 6

Met Gly Leu Thr Tyr Gln Leu Leu Pro Ala Leu Val Cys Leu Leu Ala
1               5                   10                  15

Cys Thr Ser Asn Phe Ile Gln Gly Cys Lys Tyr Asp Ile Thr Leu Gln
            20                  25                  30
```

```
Glu Ile Ile Lys Thr Leu Asn Asn Leu Thr Asp Gly Lys Gly Lys Asn
        35                  40                  45

Ser Cys Met Glu Leu Thr Val Ala Asp Ala Phe Ala Gly Pro Lys Asn
    50                  55                  60

Thr Asp Gly Lys Glu Ile Cys Arg Ala Ala Lys Val Leu Gln Gln Leu
65                  70                  75                  80

Tyr Lys Arg His Asp Arg Ser Leu Ile Lys Glu Cys Leu Ser Gly Leu
                85                  90                  95

Asp Arg Asn Leu Lys Gly Met Ala Asn Gly Thr Cys Cys Thr Val Asn
                100                 105                 110

Glu Ala Lys Lys Ser Thr Leu Lys Asp Phe Leu Glu Arg Leu Lys Thr
            115                 120                 125

Ile Met Arg Glu Lys Tyr Ser Lys Cys
        130                 135

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide sequence representing the
      enterokinase cleavage site

<400> SEQUENCE: 7

Asp Asp Asp Asp Lys
1               5
```

STIMULATION OF NEONATAL IMMUNITY AGAINST EHV-1

CROSS REFERENCE TO RELATED APPLICATION

This application claims the benefit of priority to U.S. Provisional Application Ser. No. 61/903,619, filed on Nov. 13, 2013, which is incorporated by reference into the present application.

INCORPORATION BY REFERENCE OF SEQUENCE LISTING

The Sequence Listing in the ASCII text filed, named as 30621_6465_03_US_Sequence Listing.txt of 7 kilobytes, created on May 12, 2016, and submitted to the United States Patent and Trademark Office via EFS-Web, is incorporated herein by reference.

FIELD OF THE INVENTION

The present invention relates to methods for inducing an immune response to a pathogen in neonatal mammals. In particular, the present invention relates to methods for inducing an immune response to a pathogen in a neonatal mammal comprising administering to the neonatal mammal a composition comprising a fusion protein between interleukin-4 (IL-4) and a first antigen of the pathogen.

BACKGROUND OF THE INVENTION

Typically, vaccines are optimized to induce immunity in adults. However, the neonatal immune system reacts differently from that of adults. Neonates are not equipped with adult-like T-helper (Th)-cell-responses. Early in life, B-cell activation follows alternative induction pathways that are Th-independent.

Using equine herpesvirus type 1 (EHV-1) as an example, a number of vaccines for prevention of EHV-1 disease, including inactivated and modified-live virus vaccines, are available in the US and Europe. Through the use of these vaccines and improved management practices, the occurrence of abortion storms has generally decreased. However, outbreaks of EHV-1 continue to occur in the face of widespread vaccination. Because very young foals react weakly to available vaccines, first vaccination is generally recommended between 4-6 months of age (American Association of Equine Practitioners, Equine Vaccination Guidelines). The first dose is followed in 4-6 weeks by the first booster and the second booster at 10-12 months of age. This recommendation is identical for inactivated and modified-live vaccines. At the time of first vaccination, maternal antibodies have almost entirely disappeared from the foal's circulation leaving a gap of several weeks during which foals are poorly protected from infection with major pathogens. For pathogens that are frequently transmitted early in life such as EHV-1, this vaccination regimen is suboptimal. Consequently, many foals are infected early in life by their dams or other foals.

All currently available EHV-1 vaccines are optimized to induce immunity in adult horses. This is mostly achieved by stimulating B-cells and antibodies via Th2-cell mediated pathways. During their interaction with B-cells, antigen-specific Th2-cells produce the cytokine interleukin-4 (IL-4), formerly known as B-cell stimulatory factor 1. IL-4 then initiates B-cell differentiation and immunoglobulin class switching which results in formation of antigen-specific memory B-cells and IgG secreting plasma cells.

T-Cell Immunity in Neonatal Mammals:

The immune responses in neonatal mammals, including, but not limited to foals differ from those in adults during the first year of life. Specifically, using neonatal foals as an illustrative example, T-cell and cytokine responses are reduced and delayed in foals for at least 3 months after birth. In addition, cellular immune responses of foals are Th1-biased. Th2-responses are almost undetectable in neonates. IL-4 production by Th2-cells increases slowly with age and does not reach adult levels until 3 months of age.

The induction of a classical Th2-response is a key mechanism of current vaccines' effects. It is thus not surprising that antibody production of young foals is fairly poor after vaccination with the currently approved EHV-1 vaccines.

Alternative Mechanisms to Produce Antibodies in Neonatal Mammals:

Although Th2-responses are impaired in neonates and young mammals, the onset of antibody production occurs almost immediately after birth. Using neonatal foals as an example, while maternal antibodies decline, endogenous IgG3/5, and IgA synthesis were detected within the first 5 to 8 weeks of life and reached adult serum levels by about 3 months of age. IgG1 production was detected by 5 weeks of age. At 2-3 months, IgG1 was up to 3-fold higher in foal than in adult serum. Only IgG4 and IgE antibodies showed a delay of endogenous production in foals, and this may functionally be compensated by the increased IgG1 concentrations. It should be noted that endogenous antibody production was measured in these studies as increase on top of residual maternal antibodies, i.e. the true onset of antibody development was even earlier. In summary, there is a clear discrepancy between the onset of antibody production and the development of Th2-immunity in foals.

The disconnection of B- and T-cell immunity early in life suggests that neonatal mammals induce antibody production by a Th2-cell independent pathway. Recent studies have shown that IL-4, a major B-cell stimulatory and antibody inducing cytokine is produced in neonatal foals by a different cell type, the basophil. IL-4 production by neonatal basophils peaked at 5 days after birth and could be induced during the first 3 months by stimulation of basophils. In adults, basophils are potent IL-4 producers. Today, various groups have shown evidence in humans or in rodent models that basophils have important immune regulatory functions for the induction of innate and adaptive immunity including the development of Th2-cells and the regulation of IgE production. However, all these studies were performed in adults.

Accordingly, there is a need for methods for inducing an immune response to a pathogen in neonatal mammals. The current invention demonstrates that the neonatal immune system, once considered to be immature, is now recognized to be specifically adapted for early postnatal life. In fact, an immediate induction of B-cell differentiation occurs by basophil-derived IL-4 in neonatal foals. Because the classical Th2-pathway of B-cell activation is virtually missing in neonatal and young foals, this alternative B-cell induction mechanism likely dominates the neonatal immune response. The identification of this pathway positively impacts and alters neonatal vaccinology beyond EHV-1 vaccination by harnessing the inherent immunity of neonates such that safer and more effective neonatal vaccines can be developed.

SUMMARY OF THE INVENTION

In one embodiment, the present invention provides a method of inducing an immune response to a pathogen in a neonatal mammal, wherein a fusion protein between interleukin-4 (IL-4) and an antigen of the pathogen is administered to the neonatal mammal. The pathogen can be, for example, equine herpesvirus type 1.

In some embodiments, the immune response can be induced without adjuvants.

In some embodiments, an IgE specific to an antigen of the pathogen may also be administered to the neonatal mammal prior to the fusion protein.

In one embodiment, the present invention provides a method of inducing an immune response to a pathogen in a neonatal mammal, wherein an IgE specific for an antigen of a pathogen is administered to the neonatal animal, followed by the antigen of the pathogen. In some embodiments, the immune response can be induced without adjuvants.

BRIEF DESCRIPTION OF THE DRAWINGS

FIG. 1 (A) depicts Th2-dependant antibody production in adult mammals. FIG. 1(B) depicts antibody production in neonatal animals.

FIG. 2 shows the mechanism by which one embodiment of the present invention stimulates antibody production in neonatal mammals.

FIG. 3 (A) shows the body temperature of weanlings infected with EHV-1 and treated according to one embodiment of the methods of the present invention. FIG. 3 (B) shows the clinical score of weanlings infected with EHV-1 and treated according to one embodiment of the methods of the present invention. FIG. 3 (C) shows the EHV-1 specific serum antibody levels in weanlings infected with EHV-1 and treated according to one embodiment of the methods of the present invention. FIG. 3 (D) shows the level of EHV-1 specific antibody levels in nasal fluid in weanlings infected with EHV-1 and treated according to one embodiment of the methods of the present invention. Animals were infected with EHV at the time indicated by the arrow. The closed circles show data obtained from animals that received 1 mg biotinylated IgE at birth, followed by 0.5 mg recombinant IL-4/EHV-1 gC antigen, conjugated with streptavidin, 2 days after birth. The half-filled circles show data obtained from animals that received 0.5 mg recombinant IL-4/EHV-1 gC antigen, conjugated with streptavidin, 2 days after birth. The open circles show data obtained from control animals.

FIG. 4 shows the SN-titer comparison in neonatal foal groups between day 2 (before EHV-1 antigen treatment) and day 5 after birth. The data was calculated from serum obtained before treatment, on day 2 after birth, and after treatment on day 5 after birth. IgE/Ag: animals that received 1 mg biotinylated IgE at birth, followed by 0.5 mg recombinant IL-4/EHV-1 gC antigen, conjugated with streptavidin, 2 days after birth. –/Ag: animals that received 0.5 mg recombinant IL-4/EHV-1 gC antigen, conjugated with streptavidin, 2 days after birth. –/–: Control animals. SN-titers on day 5 are expressed as fold-differences compared to the SN-value of each respective foal on day 2 (set as 1/dotted line).

FIG. 5 (A) shows viral shedding in foals vaccinated with gC/IL-4 fusion protein (closed circles), and non-vaccinated foals (open circles). FIG. 5 (B) shows nasal discharge in foals vaccinated with gC/IL-4 fusion protein (closed circles), and non-vaccinated foals (open circles). Viral copy numbers were measured by real-time PCR using the EHV-1 gB gene. The nasal discharge was scored by an examiner who was unaware of the vaccine groups. The p-values between the vaccinated and control horses are 0.0479 and 0.0048 for viral shedding and nasal discharge, respectively.

FIG. 6 (A) shows the level of antibodies to EHV-1 in the serum of foals vaccinated with gC/IL-4 fusion protein (closed circles), and non-vaccinated foals (open circles). FIG. 6 (B) shows the level of antibodies to EHV-1 in the nasal discharge of foals vaccinated with gC/IL-4 fusion protein (closed circles), and non-vaccinated foals (open circles). Antibodies were determined by a fluorescent bead-based assay using the EHV-1 gC antigen. The arrow shows the time of experimental infection. MFI=median fluorescent intensity; *$p<0.05$; $p<0.01$; *$p<0.001$.

FIG. 7 shows the mechanism by which one embodiment of the present invention stimulates antibody production in neonatal mammals.

DETAILED DESCRIPTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Neonatal Mammals.

In certain embodiments, the present invention provides methods and compositions for inducing an immune response in a neonatal mammal. Any neonatal mammal is suitable for vaccination using the methods and compositions of the present invention.

The term “mammal” as used herein refers to human beings, dogs, cats, cattle, sheep, goats, horses, pigs and other mammals such as alpacas, llamas, mice, and rats.

The term “neonatal” or “neonate” or “neonatal mammal” as used herein refers to a newborn infant. In certain embodiments, a neonate is an infant that lacks a Th2 immune response. In certain embodiments, a neonate is an infant that has an impaired Th2 immune response. In certain embodiments, a neonate is an infant that has a Th2 immune response that is lower than the level observed in an adult mammal. The length of time that an infant is considered a neonate may vary by the species of animal. Generally speaking a neonatal mammal is not more than five weeks old. In certain embodiments, a neonatal mammal is not more than four weeks old. In certain embodiments, a neonatal mammal is not more than three weeks old. In certain embodiments, a neonatal mammal is not more than two weeks old. In certain embodiments, a neonatal mammal is not more than ten days old. In one embodiment, a human neonate is a child less than 28 days old. In one embodiment, an equine neonate is a foal less than four weeks old. In one embodiment, a murine neonate is a pup less than ten days old.

Antigen-Specific IgE.

In certain embodiments, neonatal mammals receive an IgE specific for an antigen for a pathogen. Typically, the IgE specific for an antigen for a pathogen is from the same species as the neonatal mammal. The generation and selection of IgE specific for an antigen for a pathogen may be via any suitable method readily selected by one of skill in the art, such as, for example via the generation and screening of hybridoma cell lines. In one embodiment, equine IgE is produced using a heterohybridoma cell line, according to the methods described in KEGGAN et. al., Vet. Immunol. Immunopathol., 153: 187-193 (2013).

Pathogens and Antigens.

The term "antigen" as used herein refers to any substance that is recognized by the immune system and provokes an immune response. Antigens in general include polysaccharides, glycolipids, glycoproteins, proteins, peptides, carbohydrates and lipids from cell surfaces, cytoplasm, nuclei, mitochondria and the like. The portion of the antigen that is recognized by the immune system, and to which antibodies bind is referred to herein as the "epitope". The epitope may be all, or a portion of the antigen. Specific, non-limiting examples of an epitope include a tetra- to penta-peptide sequence in a polypeptide, a tri- to penta-glycoside sequence in a polysaccharide.

Antigens include polysaccharides, glycolipids, glycoproteins, peptides, proteins, carbohydrates and lipids from pathogens, including, but not limited to, viruses, bacteria, parasites or fungi. Examples of pathogens include *Vibrio choleras*, enterotoxigenic *Escherichia coli*, rotavirus, *Clostridium difficile*, *Shigella* species, *Salmonella typhi*, parainfluenza virus, influenza virus, *Streptococcus pneumonias, Borrelia burgdorferi*, HIV, *Streptococcus mutans, Plasmodium falciparum, Staphylococcus aureus*, rabies virus, Epstein-Barr virus, and herpes simplex virus. Specific antigens to pathogens are known to those of skill in the art, for example, influenza HA, NA, M2, HIV gp120, *Mycobacterium tuberculosis* Ag85B and ESAT6, *Streptococcus pneumonia* PspA, PsaA, and CbpA, respiratory syncytial virus (RSV) F and G protein, human papilloma virus protein, to name a few.

In one embodiment, the pathogen is a member of the subfamily Alphaherpesvirinae. In one embodiment, the pathogen is a Herpesviridae family member. This subfamily includes human pathogens as well as a number of animal viruses of considerable agricultural and economical importance. The human pathogens herpes simplex virus type 1 (HSV-1), herpes simplex virus type 2 (HSV-2) and varicella zoster virus (VZV) are the causative agents of cold sores, genital ulcerous disease, and chickenpox/shingles, respectively. In addition, HSV-1 and HSV-2 cause fatal disseminated disease in newborns.

In one embodiment, the pathogen is equine herpesvirus type 1 (EHV-1). EHV-1 is composed of an icosahedral nucleocapsid containing the viral genome, surrounded by an amorphous envelope, which contains the following glycoproteins: gB, gC, gD, gE, gG, gH, gI, gK, gL, gM, gN, and gp2. The majority of EHV-1 proteins share extensive homology with human simplex virus.

In one embodiment, the antigen is an EHV-1 glycoprotein. In one embodiment, the EHV-1 glycoprotein is selected from the group consisting of gB, gC, gD, gE, gG, gH, gI, gK, gL, gM, gN, and gp2. In one embodiment, the antigen is gC. In one embodiment, the antigen is a protein having at least 75%, 80%, 85%, 90%, 95%, 95%, 96%, 97%, 98%, 99%, 99.1%, 99.2%, 99.3%, 99.4%, 99.5%, 99.6%, 99.7%, 99.8% or 99.9% identity to gC.

In one embodiment, the antigen is a fragment of an EHV-1 glycoprotein. The term "fragment" refers to any antigen having less than the entire antigen mentioned herein that is capable of inducing an immune response. Specific, non-limiting examples of an antigen that is a fragment of an EHV-1 glycoprotein include tetra- to nona-peptide sequences of the EHV-1 glycoprotein. In one embodiment, the fragment of the EHV-1 glycoprotein is selected from the group consisting of fragments of gB, gC, gD, gE, gG, gH, gI, gK, gL, gM, gN, and gp2. In one embodiment, the antigen is a fragment of gC.

In one embodiment, the antigen may be administered to the neonatal mammal. In an alternate embodiment, the antigen may be fused to interleuklin-4 and the fusion molecule may be administered to the neonatal mammal.

A recombinant antigen can be made by creating a nucleic acid molecule encoding the antigen and expressing the antigen from such nucleic acid in a recombinant expression system. The nucleic acid molecule encoding the antigen can be generated by any suitable method, readily selected by one of skill in the art.

One of skill would recognize that modifications can be made to the antigen without diminishing its biological activity. Some modifications may be made to facilitate the cloning, expression, or incorporation of the antigen into an expression vector. For example, nucleic acid residues can be placed on either terminus to create conveniently located restriction sites, termination codons, or initiation codons.

Recombinant Expression of the Antigen:

For recombinant expression of an antigen, a nucleic acid molecule encoding the antigen is generally placed in an expression vector in an operable linkage to a promoter (such as, for example, the T7, trp, or lambda promoters for expression in bacteria, or a CMV promoter for expression in mammalian cells) and a 3' transcription termination sequence, and optionally additional suitable transcriptional and/or translational regulatory elements such as a transcription enhancer sequence and a sequence encoding suitable mRNA ribosomal binding sites. Additional sequences that can be included in the expression vector include an origin of replication, and a selection marker gene to facilitate identification of transformants such as genes conferring resistance to antibiotics (e.g., the amp, kana, gpt, neo, and hyg genes).

Host cells suitable for use in the recombinant expression of the fusion protein include bacterial cells such as *E. coli*, and eukaryotic cells including but not limited to yeast, insect cells (e.g. SF9 cells), and mammalian cells such COS, CHO and HeLa cells.

The expression vectors can be introduced into a host cell by well-known methods such as calcium chloride transformation for bacterial cells, and calcium phosphate treatment or electroporation for mammalian cells. Cells transformed by the expression vectors can be selected based on the phenotype provided by the selectable marker gene.

Once expressed, the recombinant antigen can be purified according to standard methods available in the art, such as ammonium sulfate precipitation, affinity columns, chromatography, gel electrophoresis, among others. While it is preferred that the antigen be subjected to a purification procedure such that a partially or highly purified preparation of the antigen is used for immunization, a crude preparation of the antigen can also be used in the methods of the present invention when used at a higher amount of total protein. By "partially purified" is meant that the antigen constitutes at least 50%, 60% or 70% of the total proteins in a protein preparation. Purities such as 75%, 80%, 90%, 95% or higher can be achieved and are preferred.

Fusion Protein.

A fusion protein between IL-4 and an antigen to the pathogen can be made by creating a nucleic acid molecule encoding the fusion protein and expressing the fusion protein from such nucleic acid in a recombinant expression system. The nucleic acid molecule encoding the fusion can be generated by linking a nucleic acid sequence encoding IL-4 in frame with the nucleic acid sequence encoding the antigen.

In one embodiment, IL-4 is fused to the N-terminus of the antigen. In this orientation, IL-4 can be used as an N-terminal tag for detection and purification of the fusion protein. In addition, when the full length IL-4 coding sequence is used, the leader sequence (secretory signal peptide) of the cytokine can facilitate the secretion of the IL-4/antigen fusion protein. Alternatively, other appropriate leader sequences, suitable for guiding the IL-4/antigen fusion protein to the ER and the secretory pathway in the host cell, can be used instead of the leader sequence of IL-4 and linked to the mature sequence of IL-4.

In another embodiment, IL-4 is fused to the C-terminus of the antigen. In making a fusion of this orientation, preferably the mature form of IL-4, rather than the full-length sequence including the leader sequence, is used. The fusion protein can rely on the leader sequence of the antigen if present, or a heterologous leader sequence (from a protein other than the antigen) functional in the host cell, to achieve secretion of the fusion protein.

Figure 7:
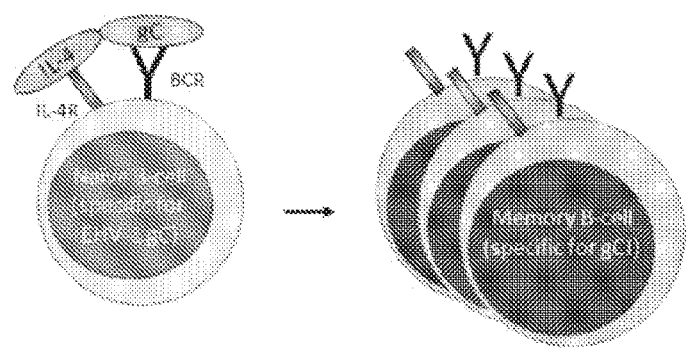

In still another embodiment, a spacer can be incorporated between IL-4 and the antigen. By "spacer" is meant a short peptide sequence that joins IL-4 and the antigen, yet preserves some distance between the two proteins such that both IL-4 and the antigen can properly fold independently. Generally, the spacer consists of between 2 or 3 amino acids to 50 amino acids, typically between 3 to 25, or 3 to 20, or 3 to 15 amino acids. In a specific embodiment, the space consists of 3-10 amino acids. Although there is no specific restriction on the selection of amino acids for the spacer region, the amino acids can be selected to accommodate the folding, net charge, hydrophobicity or other properties of the fusion protein. Typical amino acids for use in a spacer region include Gly, Ala, Ser, Thr and Asp.

The protein and nucleic acid sequences for IL-4 have been identified from a variety of animal species and are available through, e.g., GenBank database. As illustration, SEQ ID NOS: 1-6 set forth the protein and amino acid sequences of full-length human, murine and equine IL-4.

Nucleic acid sequences encoding either the full-length form or the mature form (i.e., the full-length minus the signal or leader peptide) of IL-4 can be used in making a fusion protein. In some embodiments, naturally-occurring IL-4 is used in making fusion proteins. It should be recognized that allelic variations may exist for IL-4 within an animal species; i.e., there might be several naturally-occurring (wild type) allelic sequences for IL-4, all of which are suitable for use in making the fusion protein of the invention. In other embodiments, mutant or genetically modified forms of IL-4 is used as long as the mutant forms substantially retain the activity (e.g., binding to receptor, and/or stimulation of B cells) of the wild type IL-4. By "substantially" is meant at least 75%, 80%, 85%, 90%, 95% or greater.

In one specific embodiment, the spacer region includes a cleavage site recognized by a protease. If desirable, IL-4 and the antigen can be separated from each other by protease cleavage after recombinant expression and purification. An example of a cleavage site is the enterokinase (EK) cleavage site, $(Asp)_4$-Lys (SEQ ID NO: 7).

In another embodiment, the nucleotide sequence encoding the spacer is designed to include one or more endonuclease restriction sites which facilitate the formation and cloning of the fusion protein.

One of skill would recognize that modifications can be made to IL-4, an antigen or the fusion protein without diminishing their biological activities. Some modifications may be made to facilitate the cloning, expression, or incorporation of the constituent molecules into a fusion protein. For example, nucleic acid residues can be placed on either terminus to create conveniently located restriction sites, or termination codons, or initiator codons.

Recombinant Expression of the Fusion Protein:

For recombinant expression of a fusion protein, a nucleic acid molecule encoding the fusion protein is generally placed in an expression vector in an operable linkage to a promoter (such as, for example, the T7, trp, or lambda promoters for expression in bacteria, or a CMV promoter for expression in mammalian cells) and a 3' transcription termination sequence, and optionally additional suitable transcriptional and/or translational regulatory elements such as a transcription enhancer sequence and a sequence encoding suitable mRNA ribosomal binding sites. Additional sequences that can be included in the expression vector include an origin of replication, and a selection marker gene to facilitate identification of transformants such as genes conferring resistance to antibiotics (e.g., the amp, kana, gpt, neo, and hyg genes).

Host cells suitable for use in the recombinant expression of the fusion protein include bacterial cells such as *E. coli*, and eukaryotic cells including but not limited to yeast, insect cells (e.g. SF9 cells), and mammalian cells such COS, CHO and HeLa cells.

The expression vectors can be introduced into a host cell by well-known methods such as calcium chloride transformation for bacterial cells, and calcium phosphate treatment or electroporation for mammalian cells. Cells transformed by the expression vectors can be selected based on the phenotype provided by the selectable marker gene.

Once expressed, the recombinant fusion proteins can be purified according to standard methods available in the art, such as ammonium sulfate precipitation, affinity columns, chromatography, gel electrophoresis, among others. In one embodiment, the fusion protein is purified based on affinity chromatography using antibodies specific for IL-4 in the fusion protein. While it is preferred that the fusion protein be subjected to a purification procedure such that a partially or highly purified preparation of the fusion protein is used for immunization, a crude preparation of the fusion protein can also be used in the methods of the present invention, when used at a higher amount of total protein. By "partially purified" is meant that the fusion protein constitutes at least 50%, 60% or 70% of the total proteins in a protein preparation. Purities such as 75%, 80%, 90%, 95% or higher can be achieved and are preferred. By using affinity columns, the purity is usually at least 90%.

In one embodiment, the fusion protein is generated and expressed according to the methods described in U.S. patent application Ser. No. 13/115,282.

Inducing an Immune Response to a Pathogen in a Neonatal Mammal.

In one embodiment, the present invention provides a method of inducing an immune response to a pathogen in a neonatal mammal by administering to the neonatal mammal a fusion protein between interleukin-4 (IL-4) and a first antigen of the pathogen.

Without limiting to any particular theory, it is believed that IL-4 in the fusion protein directly and selectively influences the development of antigen-specific B-cell clones. For example, the boosting effect of IL-4/antigen fusion protein is believed to result from a targeted stimulation of exactly those naïve B-cells that recognize the antigen, and IL-4/antigen fusion protein is able to bridge the B-cell receptor (BCR) and the IL-4 receptor (IL-4R) expressed on naïve B-cells (FIG. 7). Thus, the fusion protein stimulates the maturation and antibody production by those B-cell clones that specifically recognize the antigen.

In one embodiment, the pathogen is equine herpevirus type 1 (EHV-1). Antigens for EHV-1 include an EHV-1 glycoprotein selected from the group consisting of gB, gC, gD, gE, gG, gH, gI, gK, gL, gM, gN, and gp2. In one embodiment, the antigen is gC.

In one embodiment, the immune response can be induced by a fusion protein without adjuvants.

The term "adjuvant" as used herein, refers to any substance that nonspecifically potentiates the immune response to an antigen. Adjuvants include aluminum compounds, e.g., gels, aluminum hydroxide and aluminum phosphate, and Freund's complete or incomplete adjuvant (in which the fusion protein is incorporated in the aqueous phase of a stabilized water in paraffin oil emulsion). The paraffin oil may be replaced with different types of oils, e.g., squalene or peanut oil. Other materials with adjuvant properties include, flagellin, BCG (attenuated *Mycobacterium tuberculosis*), calcium phosphate, levamisole, isoprinosine, polyanions (e.g., poly A:U) leutinan, pertussis toxin, cholera toxin, lipid A, saponins and peptides, e.g. muramyl dipeptide. dimethyl dioctadecyl-ammonium bromide (DDA); monophosphoryl lipid A (MPL); LTK63, lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, Montanide ISA-51, ISA-720, microparticles, immunostimulatory complexes, liposomes, virosomes, virus-like particles, CpG oligonucleotides, cholera toxin, heat-labile toxin from *E. coli*, lipoproteins, dendritic cells, IL-12, GM-CSF, nanoparticles including calcium phosphate nanoparticles, combination of soybean oil, emulsifying agents, and ethanol to form a nanoemulsion; ASO4, ZADAXIN, or combinations thereof.

The fusion protein between IL-4 and a first antigen of the pathogen may be administered to the neonatal mammal via any suitable route of administration, such as, for example, intramuscularly, subcutaneously, orally, intranasally, and the like. In one embodiment, the fusion protein between IL-4 and a first antigen of the pathogen is administered to the neonatal mammal intramuscularly. In an alternate embodiment, the fusion protein between IL-4 and a first antigen of the pathogen is administered to the neonatal mammal subcutaneously.

The dose of the fusion protein between IL-4 and a first antigen of the pathogen that is administered to the neonatal mammal will depend on a number of factors, including the size (mass) of the neonatal mammal, the extent of any side-effects, the particular route of administration, and the like. Preferably, the methods of the present invention administer a "therapeutically effective amount" of the fusion protein between IL-4 and a first antigen of the pathogen. A "therapeutically effective amount" refers to an amount effective, at dosages and for periods of time necessary, to achieve a desired therapeutic result, such as, the production of antibodies specific for the first antigen. The therapeutically effective amount may vary according to factors such as the weight of the neonatal mammal, the species of the neonatal mammal, and the ability of the fusion protein between IL-4 and a first antigen of the pathogen to generate an immune response, when the neonatal mammal is challenged with an antigen to the pathogen, or is exposed to the pathogen.

Generally speaking, the amount of the fusion protein between IL-4 and a first antigen of the pathogen required to achieve a therapeutic effect can be from about 0.1 mg to about 5, or, alternatively, about 4, 3, 2, 1, 0.5, 0.4, 0.3, or about 0.2 mg per dose, or, alternatively, per neonatal mammal. One of ordinary skill in the art can readily determine an appropriate dose range to induce an immune response in a neonatal mammal, based on these and other factors that are well known in the art.

In one embodiment, the amount of the dose of the fusion protein between IL-4 and a first antigen of the pathogen is 0.5 mg.

In one embodiment, the fusion protein between IL-4 and a first antigen of the pathogen is administered as a single dose from about one day to about sixteen days after birth. Alternatively, the fusion protein between IL-4 and a first antigen of the pathogen is administered as a single dose from about one day to about five days after birth. Alternatively, the fusion protein between IL-4 and a first antigen of the pathogen is administered as a single dose 48 hours after birth. Alternatively, the fusion protein between IL-4 and a first antigen of the pathogen is administered as a single dose within 48 hours after birth.

In an alternate embodiment, the fusion protein between IL-4 and a first antigen of the pathogen is administered in a first dose from about one day to about five days after birth, followed by a second dose that is administered from about eight days to about sixteen days after birth.

In one embodiment, the first dose of the fusion protein between IL-4 and a first antigen of the pathogen is an amount from about 0.1 mg to about 5, or, alternatively, about 4, 3, 2, 1, 0.5, 0.4, 0.3, or about 0.2 mg. In one embodiment, the amount of the first dose of the fusion protein between IL-4 and a first antigen of the pathogen is 0.5 mg.

In one embodiment, the second dose of the fusion protein between IL-4 and a first antigen of the pathogen is an amount from about 0.1 mg to about 5, or, alternatively, about 4, 3, 2, 1, 0.5, 0.4, 0.3, or about 0.2 mg. In one embodiment, the amount of the second dose of the fusion protein between IL-4 and a first antigen of the pathogen is 0.5 mg.

In one embodiment, the first and second doses are the same amount.

In certain embodiments, prior to the administration of the fusion protein between IL-4 and a first antigen of the pathogen, an IgE that is specific to a second antigen of the pathogen is administered to the neonatal mammal. In certain embodiments, the first and second antigens are the same.

In one embodiment, the pathogen is equine herpevirus type 1 (EHV-1). Antigens for EHV-1 include an EHV-1 glycoprotein selected from the group consisting of gB, gC, gD, gE, gG, gH, gI, gK, gL, gM, gN, and gp2. In one embodiment, the antigen is gC.

The IgE that is specific to a second antigen of the pathogen may be administered to the neonatal mammal via any suitable route of administration, such as, for example, intramuscularly, subcutaneously, orally, intranasally, and the like. In one embodiment, the IgE that is specific to a second antigen of the pathogen is administered to the neonatal mammal orally.

The amount of the IgE that is specific to a second antigen of the pathogen can be from about 1 mg to about 20, or, alternatively, about 10, 5, 4, 3, or about 2 mg per dose, or, alternatively, per neonatal mammal. In one embodiment, the amount of the dose of the IgE that is specific to a second antigen of the pathogen is 1 mg.

In one embodiment, the IgE that is specific to a second antigen of the pathogen is administered as a single dose from about one hour to about eighteen hours after birth. Alternatively, the IgE that is specific to a second antigen of the pathogen is administered as a single dose within eight hours after birth. Alternatively, the IgE that is specific to a second antigen of the pathogen is administered as a single dose within six hours after birth.

In certain embodiments, the fusion protein between IL-4 and a first antigen of the pathogen is administered within 72 hours after the IgE that is specific to a second antigen of the pathogen. In one embodiment, the fusion protein between IL-4 and a first antigen of the pathogen is administered within 48 hours after the IgE that is specific to a second antigen of the pathogen. In one embodiment, the IgE that is specific to a second antigen of the pathogen is administered as a single dose within six hours after birth, and fusion protein between IL-4 and a first antigen of the pathogen is administered two days after birth.

In one embodiment, both the fusion protein between IL-4 and a first antigen of the pathogen, and the IgE that is specific to a second antigen of the pathogen are administered within eight hours after birth.

In one embodiment, the present invention provides a method of inducing an immune response to a pathogen in a neonatal mammal, wherein an IgE specific for an antigen of a pathogen is administered to the neonatal animal, followed by the antigen of the pathogen. In some embodiments, the immune response can be induced without adjuvants.

In one embodiment, the pathogen is equine herpevirus type 1 (EHV-1). Antigens for EHV-1 include an EHV-1 glycoprotein selected from the group consisting of gB, gC, gD, gE, gG, gH, gI, gK, gL, gM, gN, and gp2. In one embodiment, the antigen is gC.

The IgE that is specific to the antigen of the pathogen may be administered to the neonatal mammal via any suitable route of administration, such as, for example, intramuscularly, subcutaneously, orally, intranasally, and the like. In one embodiment, the IgE that is specific to the antigen of the pathogen is administered to the neonatal mammal orally.

The amount of the IgE that is specific to the antigen of the pathogen can be from about 1 mg to about 20, or, alternatively, about 10, 5, 4, 3, or about 2 mg per dose, or, alternatively, per neonatal mammal. In one embodiment, the amount of the dose of the IgE that is specific to the antigen of the pathogen is 1 mg.

In one embodiment, the IgE that is specific to the antigen of the pathogen is administered as a single dose from about one hour to about eighteen hours after birth. Alternatively, the IgE that is specific to the antigen of the pathogen is administered as a single dose within eight hours after birth. Alternatively, the IgE that is specific to the antigen of the pathogen is administered as a single dose within six hours after birth.

Generally speaking, the amount of the antigen required to achieve a therapeutic effect can be from about 0.1 mg to about 5, or, alternatively, about 4, 3, 2, 1, 0.5, 0.4, 0.3, or about 0.2 mg per dose, or, alternatively, per neonatal mammal. One of ordinary skill in the art can readily determine an appropriate dose range to induce an immune response in a neonatal mammal, based on these and other factors that are well known in the art.

In one embodiment, the amount of the dose of the antigen is 0.5 mg.

In one embodiment, the antigen administered as a single dose from about one day to about sixteen days after birth. Alternatively, the antigen is administered as a single dose from about one day to about five days after birth. Alternatively, the antigen is administered as a single dose 48 hours after birth. Alternatively, the antigen is administered as a single dose within 48 hours after birth.

In an alternate embodiment, the antigen is administered in a first dose from about one day to about five days after birth, followed by a second dose that is administered from about eight days to about sixteen days after birth.

In one embodiment, the first dose of the antigen is an amount from about 0.1 mg to about 5, or, alternatively, about 4, 3, 2, 1, 0.5, 0.4, 0.3, or about 0.2 mg. In one embodiment, the amount of the first dose of the antigen is 0.5 mg.

In one embodiment, the second dose of the antigen is an amount from about 0.1 mg to about 5, or, alternatively, about 4, 3, 2, 1, 0.5, 0.4, 0.3, or about 0.2 mg. In one embodiment, the amount of the second dose of the antigen is 0.5 mg.

In one embodiment, the first and second doses are the same amount.

In one embodiment, the present invention provides a vaccine composition that includes a fusion protein between IL-4 and a first antigen of a pathogen. In one embodiment, the vaccine composition additionally includes an IgE that is specific to a second antigen of the pathogen.

In an alternate embodiment, the present invention provides a vaccine composition that includes a first antigen of a pathogen. In one embodiment, the vaccine composition additionally includes an IgE that is specific to a second antigen of the pathogen.

The fusion proteins and IgE molecules can be provided in formulations suitable for administration. Suitable formulations include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use.

The present description is further illustrated by the following examples, which should not be construed as limiting in any way. The contents of all cited references (including literature references, issued patents, and published patent applications as cited throughout this application) are hereby expressly incorporated by reference.

EXAMPLES

Example 1

Vaccination of Neonatal Foals

Members of the subfamily Alphaherpesvirinae, family Herpesviridae, have a narrow in vivo host range, a short replication cycle and the capacity to establish lifelong, latent infection, primarily, but not exclusively, in neurons of sensory ganglia. This subfamily includes human pathogens as well as a number of animal viruses of considerable agricultural and economical importance. The human pathogens herpes simplex virus type 1 (HSV-1), herpes simplex virus type 2 (HSV-2) and varicella zoster virus (VZV) are the causative agents of cold sores, genital ulcerous disease, and chickenpox/shingles, respectively. In addition, HSV-1 and HSV-2 cause fatal disseminated disease in newborns. Some of the animal herpesviruses can cause diseases with potentially devastating economic consequences: Infection with equine herpesvirus type 1 (EHV-1) results in respiratory disorders, abortion and neurological disorders; bovine herpesvirus type 1 (BHV-1) leads to respiratory infection and abortions in cattle; pseudorabies virus (PRV, suid herpesvirus 1) infection (Aujeszky's disease) is characterized by respiratory and neurological disorders, abortion and infertility in swine; and Marek's disease virus (MDV), an oncogenic alphaherpesvirus, causes massive immunosuppression and invariably lethal T cell lymphomas in unvaccinated chickens.

EHV-1 is member of the *Varicellovirus* genus in the Alphaherpesvirinae subfamily that is highly prevalent in most equine populations. EHV-1 has an enormous medical impact on equine industries worldwide through respiratory disease, abortion, and myeloencephalopathy that often leads to death of affected animals. The disease manifestations also have great economic impact from the resulting treatments, quarantine measures and the lost training and competition times. Most horses are first infected very early in life, usually before weaning, and after initial infection remain latently infected for life. Latently infected, lactating mares act as reservoirs of the virus and are the source of infection for their foals, which in turn infect other foals and weanlings. The virus is spread via respiratory secretions during direct contact or via contact with fomites. EHV-1 first infects the respiratory epithelium and quickly enters lymphocytes in the retropharyngeal lymphoid tissues. From there, the virus spreads systemically via a cell-associated viremia, and latency is established in CD8+ T-cells and the trigeminal ganglion. The initial infection may be subclinical or mild causing only a short fever spike, but the virus may also cause severe respiratory infection in young horses, abortion in late pregnant mares, neonatal foal death, or myeloencephalopathy. EHV-1 is reactivated from the latent state and is shed again during times of stress, and all clinical manifestations may be seen during recrudescence.

Currently, a number of vaccines for prevention of EHV-1 disease, including inactivated and modified-live virus vaccines, are available in the US and Europe. Through the use of these vaccines and improved management practices, the occurrence of abortion storms has generally decreased. However, outbreaks of EHV-1 continue to occur in the face of widespread vaccination. Because very young foals react weakly to available vaccines, first vaccination is generally recommended between 4-6 months of age (American Association of Equine Practitioners, Equine Vaccination Guidelines). The first dose is followed in 4-6 weeks by the first booster and the second booster at 10-12 months of age. This recommendation is identical for inactivated and modified-live vaccines. At the time of first vaccination, maternal antibodies have almost entirely disappeared from the foal's circulation leaving a gap of several weeks during which foals are poorly protected from infection with major pathogens. For pathogens that are frequently transmitted early in life such as EHV-1, this vaccination regimen is suboptimal. Consequently, many foals are infected early in life by their dams or other foals.

Horses:

Fifteen newborn Icelandic Horse foals were enrolled in this example. Iceland is free of EHV-1, and consequently, the neonatal foals did not obtain EHV-1 specific antibodies from their dams via colostrum. The fifteen foals were divided into three groups with five foals each. This allowed the determination of the foal's endogenous EHV-1 immune response in the absence of maternal EHV-1 specific immunity.

Equine IgE:

Purified equine IgE was produced using a heterohybridoma cell line, according to the methods described in KEGGAN et. al., Vet. Immunol. Immunopathol., 153: 187-193 (2013). After purification, the equine IgE was conjugated to biotin.

Cloning and Expression of IL-4/EHV-1 gC Antigen Fusion Protein:

Glycoproteins C (gC) from EHV-1 strain Ab4 (NCBI accession AY665713) was used for expression cloning. The extracellular regions of gC (corresponding to amino acid (aa) residues 30-431) was cloned into a mammalian pcDNA3.1-based vector (Invitrogen, Carlsbad, Calif.) containing the equine IL-4 gene as previously described (WAGNER et. al, Vet. Immunol. Immunopathol., 146: 125-134 (2012)). Chinese hamster ovary (CHO) cells were transfected with purified linear DNA from each construct using the Geneporter II transfection reagent (Gene Therapy Systems, San Diego, Calif., USA). Transfected CHO cells were subsequently plated into 96-well plates for G418 selection of stable clones. Expression of the fusion protein was monitored by intracellular anti-IL-4 staining of cells by flow cytometry (WAGNER et. al, Vet. Immunol. Immunopathol., 146: 125-134 (2012)) and by IL-4 multiplex analysis of supernatants (WAGNER et. al., Vet. Immunol. Immunopathol., 127: 242-248 (2009)). Clones with the highest secretion of the fusion protein were further purified by three rounds of limiting dilution. To collect serum free supernatants, a stable transfectant was grown until 60-70% confluent, washed with medium without FCS, and maintained for 2 weeks or until cells detached. Supernatants were finally collected and purified by FPLC using an anti-IL-4 affinity column (WAGNER et. al, Vet. Immunol. Immunopathol., 146: 125-134 (2012)). After purification, the fusion protein was conjugated to streptavidin.

Figure 2:
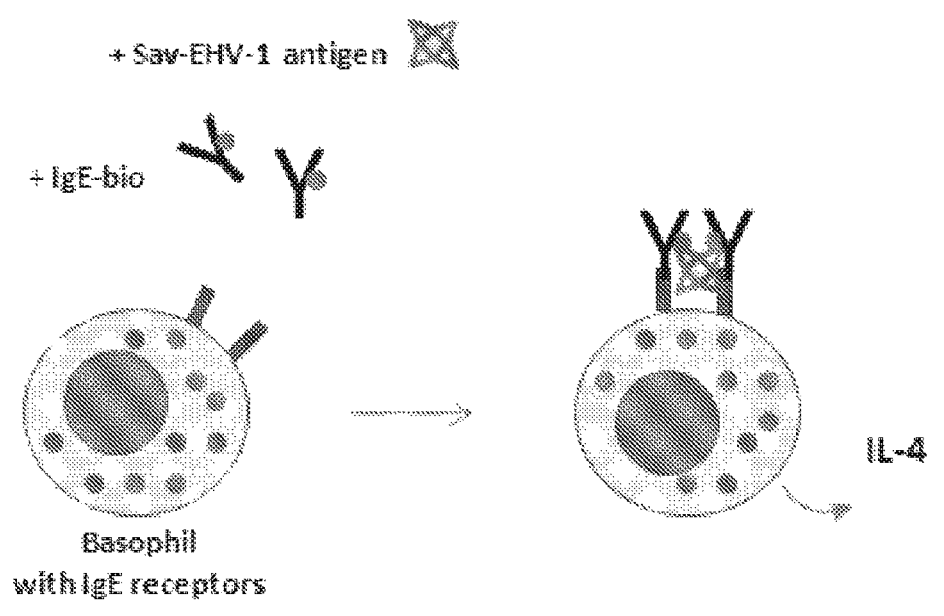

Transfer of maternal IgE antibodies to the neonate with the colostrums is known, and IgE bound to the surface of neonatal basophils is solely of maternal origin. By binding of passively transferred maternal IgE antibodies, neonatal basophils become equipped with the accumulated acquired IgE repertoire of the mare. Maternal antibodies are well known as important mediators of passive immunity providing the offspring with protection against infections until its own immune system produces sufficient amounts of antibodies. Without intending to be limited to any particular theory, it is postulated that immunization of neonatal foals by administering IgE at birth, followed by administering an EHV-1-specific antigen would induce an immune response via the induction of IL-4 production from basophils, which in turn, activates B cells. IgE binds to high-affinity IgE receptors on basophils. Normally, the circulating basophils in a neonatal foal would contain basophils that had IgE specific for EHV-1 gC, and binding of EHV-1 gG to the IgE would crosslink the IgE receptors on the basophil, thereby inducing IL-4 production. In this study, however, the animals were obtained from a population that had not been exposed to EHV-1. Consequently, there were no IgE antibodies specific for EHV-1 gC. Instead, crosslinking of the IgE receptor was mediated by a biotin-streptavidin interaction between biotinylated IgE bound to IgE receptor, and streptavidin-conjugated antigen. IgE binds to high-affinity IgE receptors on basophils. The cross-linking of the biotinylated IgE (IgE-bio) by streptavidin (Sav)-EHV-1 antigen leads to IL-4 production from the cells. IL-4 is a B-cell stimulatory factor that induces B-cell differentiation into memory and plasma cells as well as class-switching to IgG. IL-4 production from basophils can also be induced by using EHV-1-specific IgE and unconjugated EHV-1 antigen. See FIG. 2.

The neonatal animals in Group 1 received biotinylated equine IgE at within 6 hours after birth and before colostrum uptake. The biotinylated IgE was given to the neonates via nasogastric tubing in a total of 20-30 ml 0.9% saline solution. 1 mg of IgE was administered per foal. On day 2 of life, the neonatal animals in Group 1 received an intramuscular injection of 0.5 mg recombinant IL-4/EHV-1 gC antigen fusion protein conjugated with streptavidin and diluted in 1 ml PBS.

The neonatal animals in Group 2 did not receive IgE at birth. On day 2 of life, the neonatal animals in Group 2 received an intramuscular injection of 0.5 mg recombinant IL-4/EHV-1 gC antigen fusion protein conjugated with streptavidin and diluted in 1 ml PBS.

The neonatal animals in Group 3 neither received neither IgE, nor antigen.

Experimental Infection at Weanling Age:

At 7 months of age, the foals were weaned and moved to a separate pasture where they could visualize the dams. Two days later (d-2), they were moved into a separate isolation barn with individual box stalls and allowed to acclimate for a day. The stalls did not allow the horses to have direct nose-to-nose contact. However, the barn had a center hallway with the same airspace and horses were handled in the facility as one group and no other specific care was taken to prevent spread of virus from horse-to-horse by animal handlers. Biosecurity precautions were taken by people upon entering and exiting the facility. Baseline serum and nasal secretion samples were taken the day before EHV-1 infection (d-1). Baseline physical examination measurements were taken immediately before EHV-1 infection (d0).

All horses were infected intranasally with $1\times10^7$ plaque-forming units (PFU) of EHV-1 strain NY03 (d0) in 7 ml of saline using a 20 ml syringe attached to a short length (approximately 5") mucosal atomizer device (Wolfe Tory Medical, Salt Lake City, Utah). The EHV-1 strain NY03 does not possess the D752 single nucleotide polymorphism and is typed as a “non-neuropathogenic” strain (NUGENT et. al., J. Virol., 80(8): 4047-60 (2006)). All animal procedures were approved by the Institutional Animal Care and Use Committee at Cornell University.

Clinical Evaluation:

Temperatures were taken twice daily until day 7 post infection (pi) and then daily when samples were obtained. A fever was defined as a rectal temperature greater than 101.5° F. (greater than 38.6° C.). Physical examinations including neurologic scoring were performed daily until day 17 pi by an equine clinician according to a commonly used clinical scoring system described by Furr and coworkers (FURR et. al., Neurologic Examination. In: Equine Neurology. Ames, Iowa: Blackwell Publishing, 65-76 (2008)). Horses were walked daily in the isolation barn to evaluate their gait for signs of ataxia. Clinical scoring included individual scores for nasal discharge (0=none; 1=mild, serous; 2=moderate, serous; 3=mild, discolored; 4=moderate discolored; 5=mild muco-purulent; 6=moderate muco-purulent), eye discharge (0=nothing; 1=mild; 2=moderate; 3=severe) and mandibular lymph nodes (0=normal, 1=slight enlargement+/−pain on palpation, 2=moderate enlargement, 3=severely enlarged).

Samples:

Blood samples and nasal swabs were obtained on days −1, 1 to 10, 12, 14, 19, 26 and 40 pi. Blood was drawn into 10-ml tubes containing sodium heparin and into 10-ml serum tubes. Peripheral-blood mononuclear cells (PBMC) were isolated from the heparinized blood by density gradient centrifugation (Ficoll-Paque™ Plus, GE Healthcare, Piscataway, N.J.). PBMC aliquots were used immediately for virus isolation and for cellular stimulation assays to detect cytokines and EHV-1-specific T-cells, as described below. Blood in the serum tubes was allowed to clot and after centrifugation (3,000×g, RT, 15 min), serum was collected and frozen at −20° C. for later determination of EHV-1 antibodies and cytokines in serum.

Nasal swabs were obtained using two sterile, polyester tipped swabs (Puritan Medical Products Company, LLC, Guilford, Me.) placed in the nostril contacting the nasal mucosa for up to 2-3 seconds. The swabs were placed directly into polystyrene tubes containing 1 ml of phosphate buffered saline (PBS). Samples were kept in the cold (4-10° C.), transported to laboratory where they were centrifuged at 200×g for 10 min at 4° C. and stored immediately afterwards in two aliquots at −80° C. One aliquot containing the pellet plus 200 μl of the solution above the pellet was used for EHV-1 PCR. The other aliquot of the PBS/nasal sample solution was used for EHV-1 specific immunoglobulin determination and cytokine detection as described below.

EHV-1 PCR:

DNA was isolated from nasal swab samples (pellet including 200 μl PBS solution) to determine viral genome copy numbers in nasal secretions by quantitative PCR targeting the gB gene (ELIA et. al., J. Virol. Meth. 133: 70-75 (2006)). The quantitative PCR was performed at the Animal Health Diagnostic Center at Cornell University.

Virus Isolation:

Virus isolation was performed by co-cultivation of PBMC with immortalized equine kidney cells (Kindly provided by Dr. Edward Dubovi, Cornell University), and viremia scores given to each individual horse as follows: a score of 0 indicates that no virus was isolated, a score of 1 indicates that plaques were observed using $5\times10^6$ PBMC, and a score of 3 indicates plaque observation using as low as $5\times10^4$ PBMC. According to previous EHV-1 experimental infection studies, viremia was expected between days 4-9 pi (GOODMAN et. al., Vaccine, 24: 3636-3645 (2006); SOBOLL-HUSSEY et. al., Vet. Res. 42: 23 (2011)).

Detection of EHV-1 gC Specific Antibodies by a Fluorescent Bead-Based Assay:

EHV-1 multiplex analysis was performed using fluorescent beads and the Luminex system (Luminex Corp., http://www.luminexcorp.com). The EHV-1 gC antigens were coupled to beads 34, respectively, using a bead coupling procedure previously described in detail (Wagner and Freer 2009). A total of 40 μg of recombinant gC antigen was used per $5\times10^6$ beads.

All serum samples and controls were diluted 1:400 in PBN blocking buffer (PBS with 1% (w/v) BSA and 0.05% (w/v) sodium azide). Three control serum samples from horses of known EHV-1 antibody status were included in each assay. The negative serum control typically resulted in a median fluorescent intensity (MFI) of 120 for antibodies to gC. The moderately positive serum control had a MFI of 4500 and the high positive serum resulted in a MFI of 13000. Nasal secretion samples (nasal swabs and washes) were tested without dilution. Millipore Multiscreen HTS plates (Millipore, Danvers, Mass.) were soaked with PBS-T (PBS with 0.02% (v/v) Tween 20 for at least 2 minutes. After aspirating the PBST, 50 μl of the diluted serum samples and control sera were added. Wells with plain PBN were used as blank control values for the assay. The gC beads were vortexed and sonicated for 20 seconds, and 50 μl bead solution containing $5\times10^3$ gC beads were added per assay well. The plate was covered to protect it from light and was incubated at room temperature with shaking for 30 min. Plates were washed using the Biotek ELx50 plate washer (Biotek Instruments Inc., Winooski, Vt.). Then, 50 µl of a biotinylated goat anti-horse IgG(H+L) antibody (Jackson Immunoresearch Laboratories, West Grove, Pa.) was added to the plate at 1:10000 in PBN. The plate was incubated as above and washed afterwards. Another 50 µl of streptavidin-phycoerythrin (PE) (Invitrogen, Carlsbad, Calif.) were added to each well at a dilution of 1:100 in PBN and were incubated as above and washed afterwards. Finally, 100 µl of PBN were added to each well, the plate was covered and placed on a shaker for 15 minutes to re-suspend the beads. The assay was analyzed in a Luminex 200 instrument (Luminex Corp.) using BioPlex Manager 6.1 software (Bio-Rad, Hercules, Calif.). Results were reported as MFI. The assay was previously validated using EHV-1 serum neutralization (SN) titers as a gold standard. SN titers from 58 serum samples ranged from 1 to 768 (median 64). The comparison of SN-titers with continuous results from the gC assay indicated a high correlation between the assay results ($r_{sp}$=0.87; 95% CI=0.79-0.93; p<0.0001).

EHV-1-Specific Immunoglobulin Isotypes Detection:

For isotype detection, the EHV-1 gC assay described above was slightly modified. First, the nasal secretion samples (swab samples only) were run at a dilution of 1:2 in PBN blocking buffer. Second, instead of the polyclonal detection antibody monoclonal antibodies (mAbs) to equine IgM, IgG1, IgG1/3, IgG4/7, IgG3/5, IgG6 and IgA were used for detection. All mAbs were biotinylated. The mAbs were diluted as follows: anti-IgM, clone 1-22 (1:1000); anti-IgG1, clone CVS45 (1:500); anti-IgG1/3, clone 159-4 (1:500); anti-IgG4/7, clone CVS39 (1:1000); anti-IgG3/5, clone 586 (1:100); anti-IgG6, clone 267 (1:100); and anti-IgA, clone 135 (1:100). The mAbs and their use for equine immunoglobulin isotyping were previously described (Keggan et al. 2013). All other steps of the assay remained the same as described above.

Figure 3:
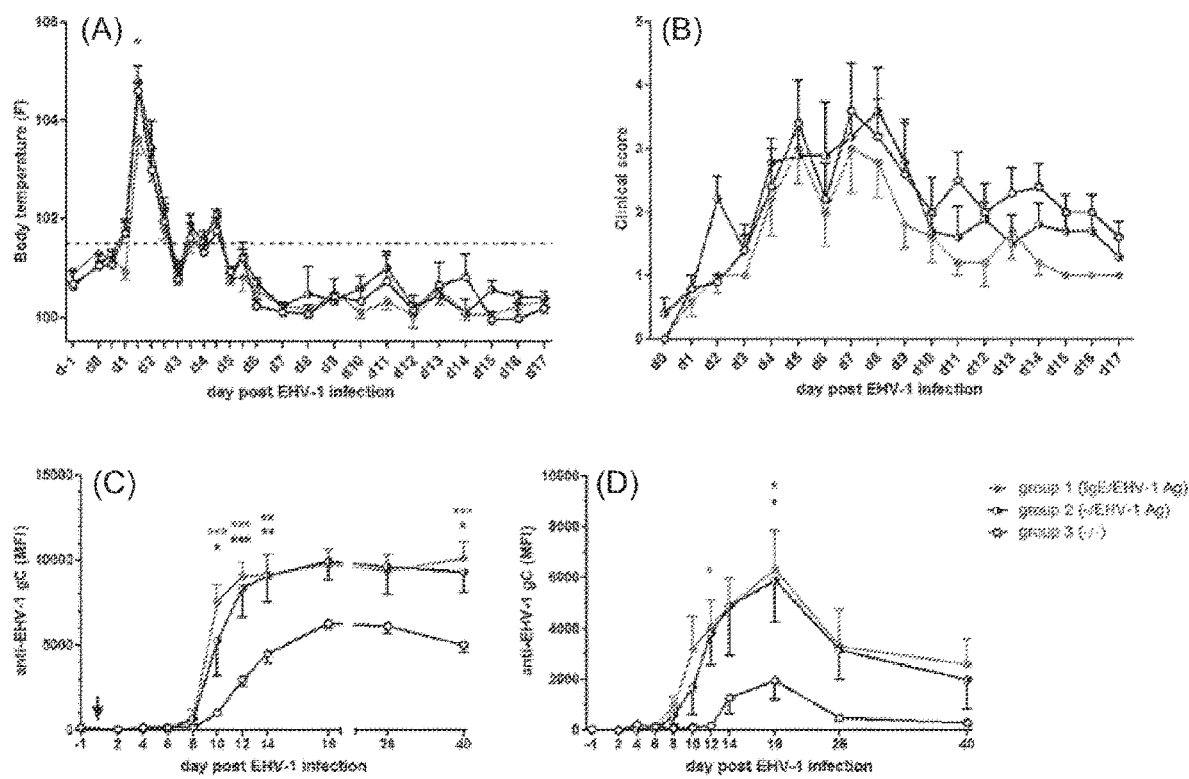

Results:

FIG. 3 shows body temperatures and antibody production in weanlings that were experimentally infected with the EHV-1 strain NY03. Neonatal foals were treated according to the treatment protocols outlined for Groups 1-3 above. Briefly, Group 1: 1 mg biotinylated equine IgE within 6 hours after birth and before colostrum uptake, followed by 0.5 mg recombinant IL-4/EHV-1 gC antigen fusion protein conjugated with streptavidin, on day 2 of life (closed circles). Group 2: 0.5 mg recombinant IL-4/EHV-1 gC antigen fusion protein conjugated with streptavidin, on day 2 of life (half filled circles). Group 3: control animals (open circles). The data shown is the mean±standard error from 5 animals per group. The upper asterisks are comparisons between Group 1 and 3. The lower asterisks are the comparisons between Group 2 and 2 at the times indicated. *p<0.05, p<0.01, * p<0.001.

Figure 4:
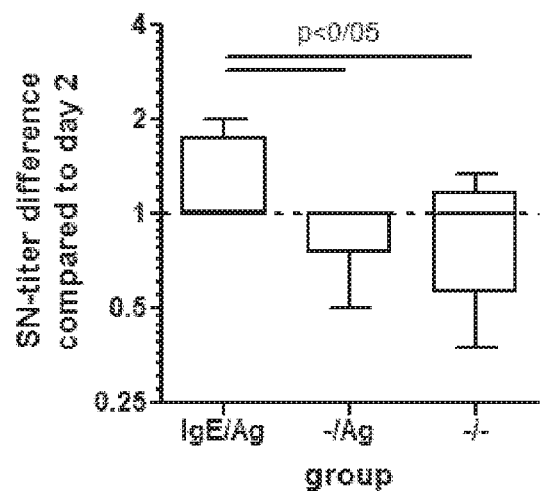
Figure 5:
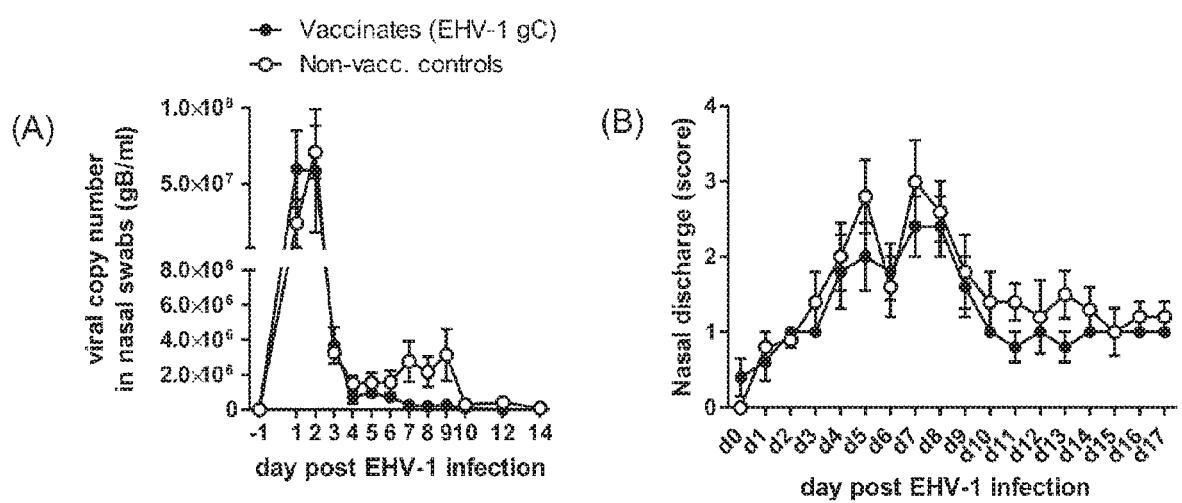
Figure 6:
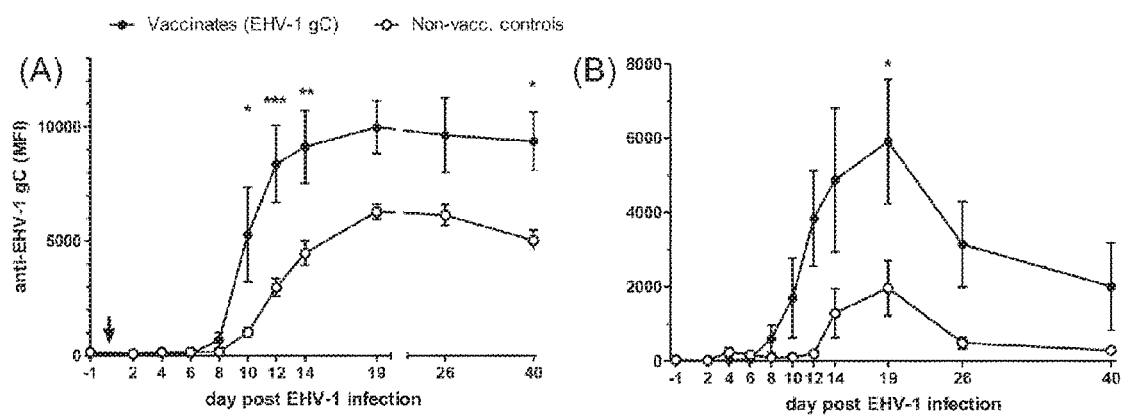

Foals that received biotinylated equine IgE at within 6 hours after birth and before colostrum uptake, followed by 0.5 mg recombinant IL-4/EHV-1 gC antigen fusion protein conjugated with streptavidin, on day 2 of life showed high antibody responses and reduced fever and clinical signs. See FIGS. 3 and 4.

After EHV-1 infection, clinical signs were most severe and antibody production was significantly lower in foals that were not vaccinated at birth. Animals from Groups 1 and 2 had comparable antibody levels and were partially protected from disease after challenge infection with EHV-1. This was an unexpected finding, as only treatment with IgE and antigen was expected to provide protection from disease. However, both Groups 1 and 2 reacted similarly. This suggested that the gC/IL-4 fusion protein (Group 2) has a similar role on B-cell activation as basophil-derived IL-4 (Group 1) and that a much simpler neonatal vaccination procedure, without the need to administer IgE, can be performed to induce immunity in neonatal foals. The results showed that a one-time dose of recombinant IL-4/EHV-1 gC antigen fusion protein at day 2 after birth provides immunity and partial protection when the foals are infected with EHV-1 at weanling age. In particular, recombinant IL-4/EHV-1 gC antigen fusion protein vaccinated foals showed reduced respiratory signs and viral shedding after experimental infection with EHV-1 (FIG. 5).

Vaccinates also had significantly higher EHV-1 gC-specific antibody levels in their serum and nasal secretions (FIG. 6). There were no differences in cellular immune parameters between the groups as tested by cytokine quantification in serum and nasal secretion, and by restimulation of PBMC followed by flow cytometric analysis of EHV-1 specific T-cells and measurement of secreted cytokines. These data suggest that the protective effects observed in the vaccinated group were due to the earlier and increased antibody production.

These data also suggested that the increased antibody levels after EHV-1 infection resulted from the single neonatal vaccination with a simple, recombinant gC/IL-4 antigen. Although there were no EHV-1-specific antibodies detected directly after birth, the vaccine procedure likely induced EHV-1-specific memory B-cells that resulted in earlier and higher antibody production at the time of EHV-1 challenge. Therefore, activation of neonatal B-cells occurs via T cell-independent mechanisms (see FIG. 7).

Without limiting to any particular theory, it is believed that IL-4 in the fusion protein directly and selectively influences the development of antigen-specific B-cell clones. For example, the boosting effect of IL-4/antigen fusion protein is believed to result from a targeted stimulation of exactly those naïve B-cells that recognize the antigen, and IL-4/antigen fusion protein is able to bridge the B-cell receptor (BCR) and the IL-4 receptor (IL-4R) expressed on naïve B-cells (FIG. 7). Thus, the fusion protein stimulates the maturation and antibody production by those B-cell clones that specifically recognize the antigen.

SEQ ID NO Description 1 human IL-4 nucleic acid sequence (NM_000589; CDS 371-832)

2 human IL-4 protein (NP_000580; the first 24 amino acids representing the signal sequence)

3 murine IL-4 nucleic acid sequence (NM_021283; CDS 60-482)

4 murine IL-4 protein (NP_067258; the first 20 amino acids representing the signal sequence)

5 equine IL-4 nucleic acid sequence (GU139701)

6 equine IL-4 protein (ACZ27799; the first 24 amino acids representing the signal sequence)

7 enterokinase cleavage site

Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method of inducing an immune response to equine herpesvirus type 1 (EHV-1) in a neonatal horse, comprising administering to the neonatal horse a first dose of a fusion protein comprising interleukin-4 (IL-4) and a first antigen of EHV-1, wherein the first antigen of EHV-1 induces the immune response in the horse, and wherein the fusion protein is administered from about one day to about five days after birth.

2. The method of claim 1, wherein the first antigen is an EHV-1 glycoprotein antigen.

3. The method of claim 2, wherein the EHV-1 glycoprotein antigen is an EHV-1 glycoprotein C (gC) antigen.

4. The method of claim 1, wherein the fusion protein is administered without an adjuvant.

5. The method of claim 1, wherein the fusion protein is administered intramuscularly.

6. The method of claim 1, wherein the fusion protein is administered subcutaneously.

7. The method of claim 1, wherein the fusion protein is administered 48 hours after birth.

8. The method of claim 1, wherein the fusion protein is administered within 48 hours after birth.

9. The method of claim 1, wherein the first dose of the fusion protein administered is from about 0.1 to about 5 mg.

10. The method of claim 1, further comprising administering a subsequent dose of the fusion protein at about eight days to about sixteen days after birth.

11. The method of claim 10, wherein the first dose is administered within 48 hours after birth, and the subsequent dose is administered from about eight days to about sixteen days after birth.

12. The method of claim 10, wherein the first dose of the fusion protein administered is from about 0.1 to about 5 mg.

13. The method of claim 10, wherein the subsequent dose of the fusion protein administered is from about 0.1 to about 5 mg.

14. The method of claim 1, wherein an IgE is administered to the neonatal horse prior to the administration of the fusion protein, and wherein the IgE is specific to a second antigen of EHV-1.

15. The method of claim 14, wherein the first antigen and the second antigen are the same.

16. The method of claim 15, wherein the antigen is an EHV-1 glycoprotein antigen.

17. The method of claim 16, wherein the EHV-1 glycoprotein antigen is an EHV-1 glycoprotein C (gC) antigen.

18. The method of claim 14, wherein the IgE is administered orally.

19. The method of claim 14, wherein the IgE is administered to the neonatal horse at about one to about eighteen hours after birth.

20. The method of claim 14, wherein the IgE is administered to the neonatal horse six hours after birth.

21. The method of claim 14, wherein the dose of the IgE administered is from about 1 mg to about 20 mg.

22. The method of claim 14, wherein the fusion protein is administered within 72 hours after the IgE.

23. The method of claim 14, wherein the fusion protein is administered within 48 hours after the IgE.

24. The method of claim 23, wherein the dose of the IgE is from about 1 mg to about 20 mg.

25. A method of inducing an immune response to EHV-1 in a neonatal horse, comprising administering to the neonatal horse (i) an IgE specific for an antigen of EHV-1, and (ii) a first dose of the antigen at about one day to about five days after birth, wherein the IgE is administered prior to the first dose of the antigen.

26. The method of claim 25, wherein the first dose of the antigen and the IgE are administered without an adjuvant.

27. The method of claim 26, wherein the antigen is an EHV-1 glycoprotein antigen.

28. The method of claim 27, wherein the EHV-1 glycoprotein antigen is an EHV-1 glycoprotein C (gC) antigen.

29. The method of claim 25, wherein the IgE is administered orally.

30. The method of claim 25, wherein the IgE is administered to the neonatal horse at about one to about eighteen hours after birth.

31. The method of claim 25, wherein the IgE is administered to the neonatal horse about six hours after birth.

32. The method of claim 25, wherein a subsequent dose of the antigen is administered at about eight days to about sixteen days after birth.

* * * * *